United States Patent [19]
Ream et al.

[11] Patent Number: 5,972,012
[45] Date of Patent: Oct. 26, 1999

[54] CUTTING APPARATUS HAVING ARTICULABLE TIP

[75] Inventors: John H. Ream, San Jose; Vahid Saadat, Redwood Shores, both of Calif.

[73] Assignee: AngioTrax, Inc., Sunnyvale, Calif.

[21] Appl. No.: 09/027,828

[22] Filed: Feb. 19, 1998

Related U.S. Application Data

[63] Continuation-in-part of application No. 08/953,046, Oct. 17, 1997, Pat. No. 5,899,915.

[51] Int. Cl.$^6$ ..................................................... A61B 17/32
[52] U.S. Cl. .............................................. 606/170; 604/22
[58] Field of Search ................................ 606/1, 167, 170, 606/171, 18; 604/22; 600/564–568

[56] References Cited

U.S. PATENT DOCUMENTS

| | | |
|---|---|---|
| 4,788,975 | 12/1988 | Shturman et al. . |
| 5,125,924 | 6/1992 | Rudko . |
| 5,125,926 | 6/1992 | Rudko et al. . |
| 5,242,460 | 9/1993 | Klein et al. . |
| 5,336,237 | 8/1994 | Chin et al. . |
| 5,358,472 | 10/1994 | Vance et al. . |
| 5,358,485 | 10/1994 | Vance et al. . |
| 5,380,316 | 1/1995 | Aita et al. . |
| 5,383,884 | 1/1995 | Summers . |
| 5,389,096 | 2/1995 | Aita et al. . |
| 5,403,334 | 4/1995 | Evans et al. . |
| 5,429,144 | 7/1995 | Wilk . |
| 5,488,958 | 2/1996 | Topel et al. . |
| 5,492,119 | 2/1996 | Abrams . |
| 5,520,634 | 5/1996 | Fox et al. . |
| 5,562,694 | 10/1996 | Sauer et al. . |
| 5,569,178 | 10/1996 | Henley . |
| 5,569,284 | 10/1996 | Young et al. . |
| 5,575,293 | 11/1996 | Miller et al. . |
| 5,575,772 | 11/1996 | Lennox . |
| 5,575,787 | 11/1996 | Abela et al. . |
| 5,591,159 | 1/1997 | Taheri . |
| 5,601,573 | 2/1997 | Fogelberg et al. . |
| 5,601,586 | 2/1997 | Fucci et al. . |
| 5,601,588 | 2/1997 | Tonomura et al. . |
| 5,607,421 | 3/1997 | Jeevanandam et al. . |
| 5,609,621 | 3/1997 | Bonner . |
| 5,611,803 | 3/1997 | Heaven et al. . |
| 5,613,972 | 3/1997 | Lee et al. . |
| 5,662,671 | 9/1997 | Barbut et al. . |

FOREIGN PATENT DOCUMENTS

WO 97/10753  3/1997  WIPO .

OTHER PUBLICATIONS

Frazier, O.H., M.D., "Myocardial Revascularization With Laser: Preliminary Findings," *Supplement II Circulation*, vol. 92, No. 9, (Nov. 1995), pp. II–58–II–65.

Hardy, Roger Ian, "A Histologic Study of Laser–Induced Transmyocardial Channels," *Lasers in Surgery and Medicine*, (1987), pp. 6:563–573.

Hershey, John E. et al., "Transmyocardial Puncture Revascularization: A Possible Emergency Adjunct to Arterial Implant Surgery," *Geriatrics*, (Mar. 1969), pp. 101–108.

Kohmoto, Takushi, M.D., "Does Blood Flow Through Holmium: YAG Transmyocardial Laser Channels?," *Ann. Thorac. Surg.*, (1996) pp. 61:861–868.

Sen, P.K. et al., "Further Studies in Multiple Transmyocardial Acupuncture as a Method of Myocardial Revascularization," *Surgery*, vol. 64, No. 5, (Nov. 1968), pp. 861–870.

White, Manuel et al., "Multiple Transmyocardial Puncture Revascularization in Refractory Ventricular Fibrillation due to Myocardial Ischemia," *The Annals of Thoracic Surgery*, vol. 6, No. 6, (Dec. 1968), pp. 557–563.

*Primary Examiner*—Michael Buiz
*Assistant Examiner*—William Lewis
*Attorney, Agent, or Firm*—Fish & Neave; Nicola A. Pisano

[57] ABSTRACT

Apparatus and methods for intraoperatively performing surgery to create transmural channels in tissue, for example, as in transmyocardial revascularization, are provided using apparatus having an end region containing a mechanical cutting head and means for articulating the end-region to access hard-to-reach portions of the anatomy. The handpiece is coupled by a disposable cable to a controller that houses a vacuum pump and mechanisms for driving the cutting head. The cutting head is adapted to cooperate with the vacuum pump to evacuate tissue severed during the channel forming process.

26 Claims, 9 Drawing Sheets

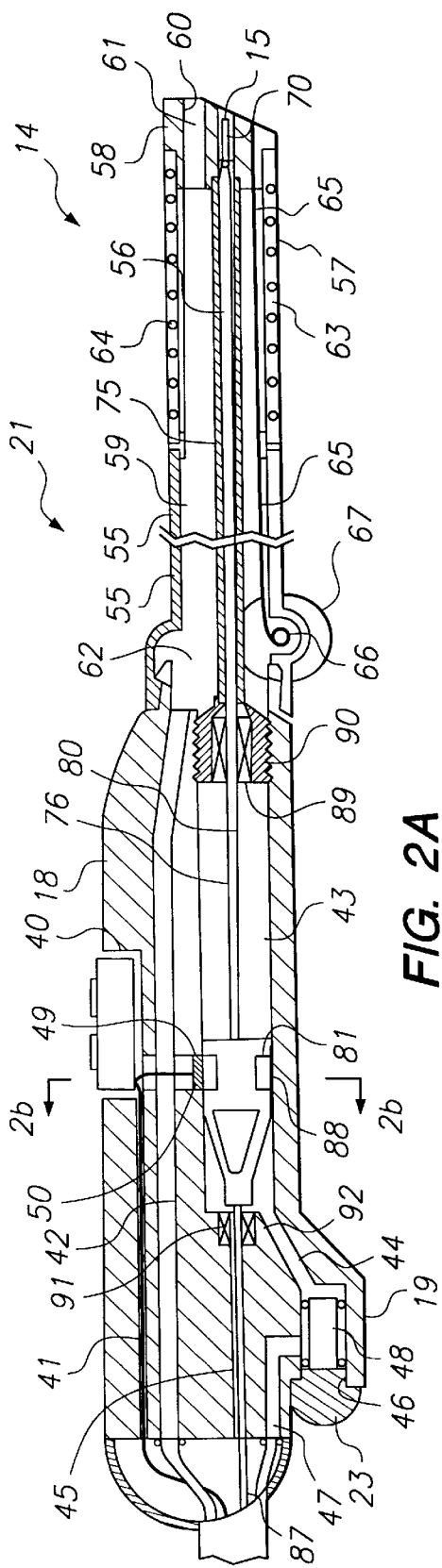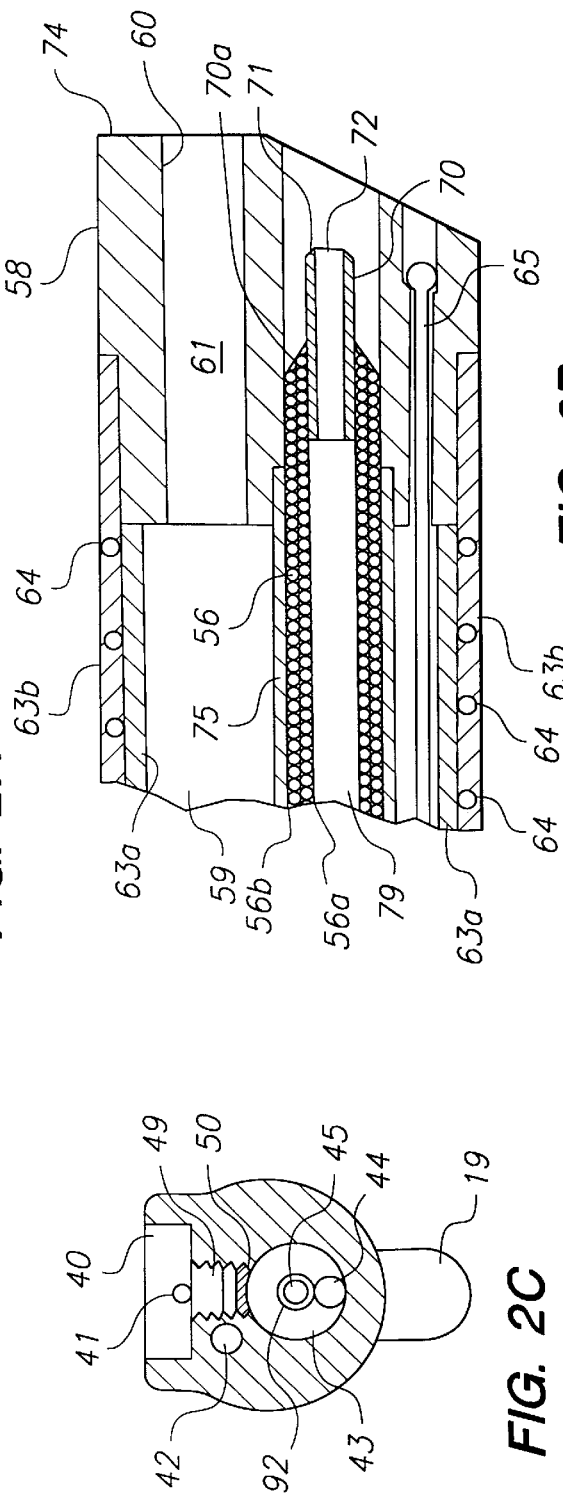
FIG. 2A
FIG. 2B
FIG. 2C

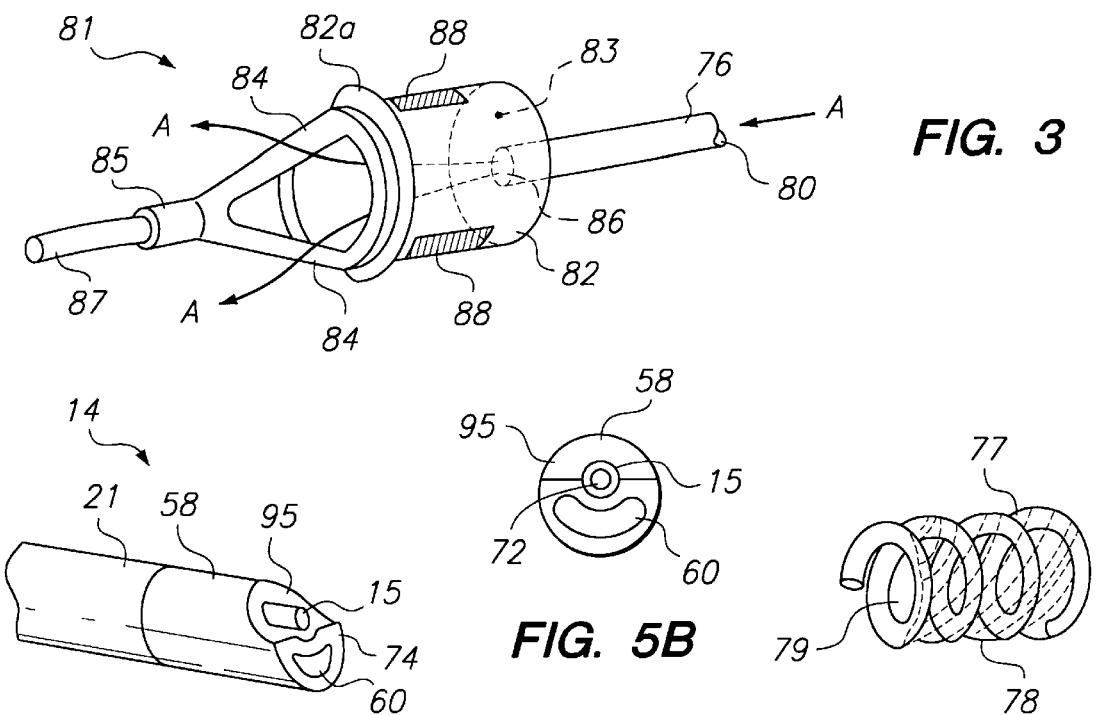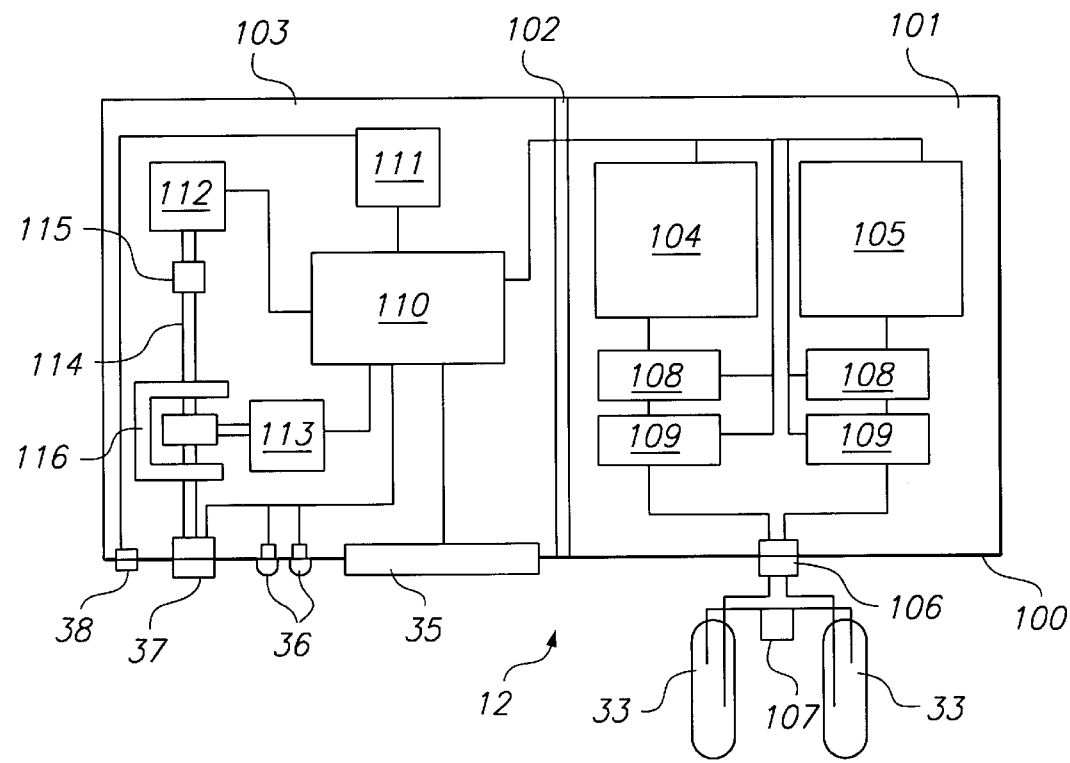

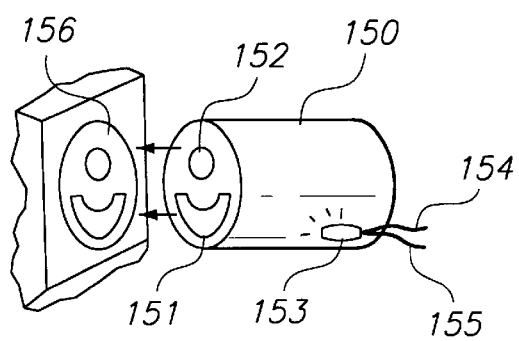
FIG. 10
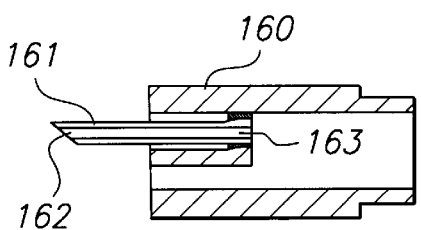
FIG. 11A
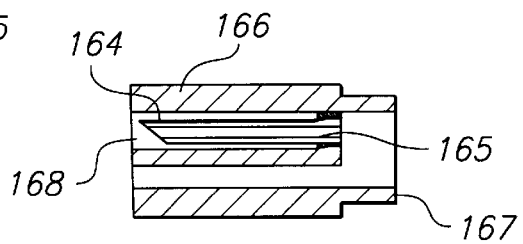
FIG. 11B
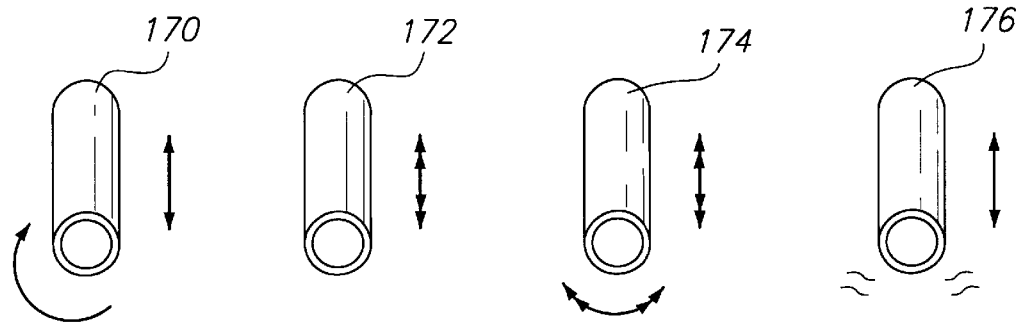
FIG. 12A    FIG. 12B    FIG. 12C    FIG. 12D
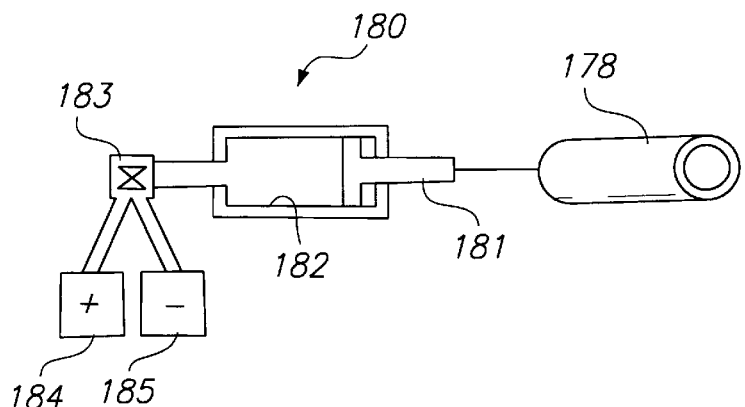
FIG. 12E
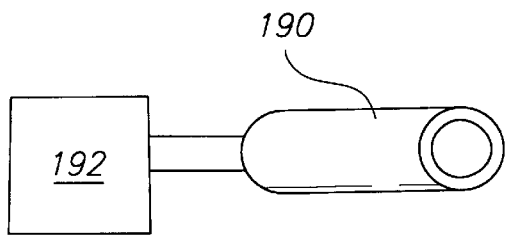
FIG. 12F

CUTTING APPARATUS HAVING ARTICULABLE TIP

REFERENCE TO RELATED APPLICATIONS

This application is a continuation-in-part of U.S. patent application Ser. No. 08/953,046, filed Oct. 17, 1997, now U.S. Pat. No. 5,899,915. The present application is also related to the subject-matter of commonly assigned U.S. patent application Ser. Nos. 08/953,769 and 08/953,782, both filed Oct. 17, 1997, both still pending.

FIELD OF THE INVENTION

The present invention relates to apparatus for forming a transmural channel in a wall of a body organ, such as the heart. More particularly, the present invention provides apparatus, including a handpiece having an articulable tip, that enables a clinician to perform transmyocardial revascularization by mechanically boring channels through the myocardium.

BACKGROUND OF THE INVENTION

A leading cause of death in the United States and the world today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery is replaced with a native artery harvested elsewhere or a synthetic graft, has been the conventional treatment for coronary artery disease for the last thirty years. Such surgery creates significant trauma to the patient, requires long recuperation times, and poses serious risks of mortality. In addition, experience has shown that the bypass vessel or graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then dilated to compress the plaque lining the artery to restore patency to the vessel. Atherectomy involves using a catheter having a mechanical cutting tip or a laser to cut (or ablate) a passage through the blockage. Such methods have drawbacks, however, ranging from re-blockage of vessels dilated by angioplasty to catastrophic rupture or dissection of the vessel during atherectomy. Moreover, these methods may only be used in larger blood vessels for that fraction of the patient population where the blockages are few and are easily accessible. Neither technique is suitable for the treatment of diffuse atherosclerosis.

A more recent technique that holds promise of treating a larger percentage of the patient population, including those patients suffering from diffuse atherosclerosis, is referred to as transmyocardial revascularization (TMR). In this method, a series of channels are formed in the left ventricular wall of the heart. These channels may be transmural (i.e., from the epicardium to the endocardium), or only partial (for example, from the endocardium and terminating in the myocardium).

Typically, between 15 and 50 channels about 1 mm in diameter and up to 3.0 cm deep are formed with a laser in the wall of the left ventricle to perfuse the heart muscle with blood coming directly from the inside of the left ventricle, rather than from the coronary arteries. It has also been proposed that the formation of such channels stimulates the creation of small blood vessels within the myocardium. Apparatus and methods have been proposed to create these channels both percutaneously and intraoperatively (i.e., with the chest opened).

U.S. Pat. Nos. 5,380,316 and 5,554,152 to Aita et al. describe intraoperative laser apparatus for forming channels extending from the epicardium to the endocardium. The laser includes an optical wave guide that is held against the patient's heart. Several pulses of the laser are required to form a transmural channel by ablation. U.S. Pat. No. 5,389,096 to Aita et al. describes a catheter-based laser system for performing TMR percutaneously, i.e., from within the left ventricle. U.S. Pat. No. 4,658,817 to Hardy describes a laser-based system for intraoperatively performing TMR that includes a needle portion for perforating an outer portion of the tissue, and a laser for ablating the inner portion.

U.S. Pat. No. 5,591,159 to Taheri describes a mechanical catheter-based apparatus for performing TMR involving a catheter having an end effector formed from a plurality of spring-loaded needles. The catheter first is positioned percutaneously within the left ventricle. A plunger then is released so that the needles are thrust into the endocardium, and the needles are withdrawn, thus forming small channels that extend into the myocardium. The patent suggests that the needles may be withdrawn and advanced repeatedly at different locations under fluoroscopic guidance. The patent does not appear to address how tissue is ejected from the needles between the tissue-cutting steps.

The disadvantages of the above-described previously known apparatus used to perform TMR are numerous and are expected to slow the acceptance of this new treatment method. For example, laser-based systems, such as described in the Aita et al. patents, require costly and sophisticated laser technology. In addition, the laser apparatus may not provide the clinician sufficient tactile sensation to judge when the endocardium has been punctured, thus creating the risk that laser pulses may be inadvertently directed against other tissue within the left ventricle before the laser is discontinued. Laser-based devices also rely on the clinician to hold the laser element steadily against the beating heart. Moreover, laser-based systems do not provide for removal of ablated tissue, thus causing a risk of embolization by ablated tissue.

Likewise, previously known mechanical systems such as described in the Taheri patent do not address issues such as rebounding of the needle away from the ventricle wall during deployment or how to remove tissue samples from the needles, and again rely on fluoroscopy to determine the location of the distal tip of the device within the heart.

In view of the shortcomings of previously known TMR devices, it would be desirable to provide apparatus for intraoperatively performing surgery, such as TMR, that uses less costly and more readily available components.

It also would be desirable to provide apparatus for performing TMR that provides the capability to precisely monitor and control the channel forming process, without a risk of inadvertently damaging other tissues within the left ventricle.

It would be desirable to provide apparatus for performing TMR that stabilizes an end region of the apparatus against a beating heart.

It further would be desirable to provide apparatus for performing TMR that enables tissue removed during the channel-forming process to be aspirated, thereby lessening the potential for embolization.

It also would be desirable to provide apparatus having an articulable end-region, to enable the clinician to form channels in posterior regions of the left ventricle.

It still further would be desirable to provide apparatus having an articulable end-region and means for viewing the target tissue and degree of articulation of the end-region when forming channels in posterior regions of the left ventricle.

SUMMARY OF THE INVENTION

In view of the foregoing, it is an object of this invention to provide apparatus for performing surgery, such as TMR, intraoperatively that uses less costly and more readily available components.

It is another object of this invention to provide apparatus for performing TMR that provides the capability to precisely monitor and control the channel forming process, without a risk of inadvertently damaging other tissues within the left ventricle.

It is a further object of the present invention to provide apparatus for performing TMR that stabilizes an end region of the apparatus against a beating heart.

It is also an object of the present invention to provide apparatus for performing TMR that enables tissue removed during the channel-forming process to be aspirated, thereby lessening the potential for embolization.

It is yet another object of this invention to provide apparatus having an articulable end-region, to enable the clinician to form channels in posterior regions of the left ventricle.

It is a still further object of the invention to provide apparatus having an articulable end-region and means for viewing the target tissue and degree of articulation of the end-region when forming channels in posterior regions of the left ventricle.

These and other objects of the present invention are accomplished by providing apparatus for intraoperatively performing TMR with a device having a handpiece including an end-region that may be selectively articulated to access posterior or other hard-to-reach surfaces of the left ventricle. The handpiece preferably includes an end region having a mechanical cutting head for forming transmural channels and means for stabilizing the end region in contact with a beating heart. The cutting head is adapted to cooperate with a source of suction to evacuate tissue severed during the channel-forming process. The handpiece may also include a fiber optic cable for viewing the target tissue and articulation of the end-region when treating posterior regions of the left ventricle.

In a preferred embodiment, the apparatus comprises a controller, a handpiece having a mechanical cutting head, and a drive cable that couples the handpiece to the controller. The controller in turn houses the mechanisms that drive the mechanical cutting head. In accordance with the present invention, the handpiece includes any of a variety of means for articulating the end-region, and thus the cutting head, of the apparatus. The mechanical cutting head preferably comprises a rotating tubular element having a central lumen through which severed tissue is aspirated, while the means for stabilizing the end region in contact with the tissue comprises a suction cup. In alternative embodiments, the cutting head may be arranged for longitudinal motion, a combination of angular and longitudinal motion, or vibratory motion.

BRIEF DESCRIPTION OF THE DRAWINGS

Further features of the invention, its nature and various advantages will be more apparent from the accompanying drawings and the following detailed description of the preferred embodiments, in which:

FIGS. 2A, 2B and 2C are, respectively, a cross-sectional elevation view of the handpiece of FIG. 1, a detailed side-sectional view of the distal end of the handpiece of FIG. 2A, and a sectional view along line 2B—2B of FIG. 2A;

FIG. 3 is a perspective view of a portion of the drive train of the handpiece of FIG. 2;

FIG. 4 is a partial perspective view of a portion of a flexible coupling used in a preferred drive train of the present invention;

FIGS. 5A and 5B are, respectively, a partial perspective and end view of the end region of the device of FIG. 2;

FIG. 6 is a schematic view of an illustrative embodiment of the controller of FIG. 1;

FIG. 10 is a partial perspective view of an alternative embodiment of the stabilization means of FIG. 2A;

FIGS. 11A and 11B are side sectional views of further alternative embodiments of the stabilization means of FIG. 2A;

FIGS. 12A to 12F are perspective views, partly in block diagram form, illustrating different cutting modalities suitable for use with apparatus constructed in accordance with the present invention;

DETAILED DESCRIPTION OF THE INVENTION

The present invention relates generally to apparatus used to perform surgery by forming a channel in a wall of an organ, and more particularly, for intraoperatively performing transmyocardial revascularization. Unlike previously known laser apparatus developed for TMR, the present invention may be implemented in apparatus having a single use handpiece that employs relatively few mechanical and electrical components.

In the following written description of the invention, illustrative embodiments are first described, and then a description of operation of the device is provided. Features suitable for use in further alternative embodiments, and optional components, are then described. As will be understood from the following description, specific components of the device may be interchanged with functionally equivalent components of the alternative embodiments set forth hereinafter to achieve the goals of the present invention.

Figure 1:
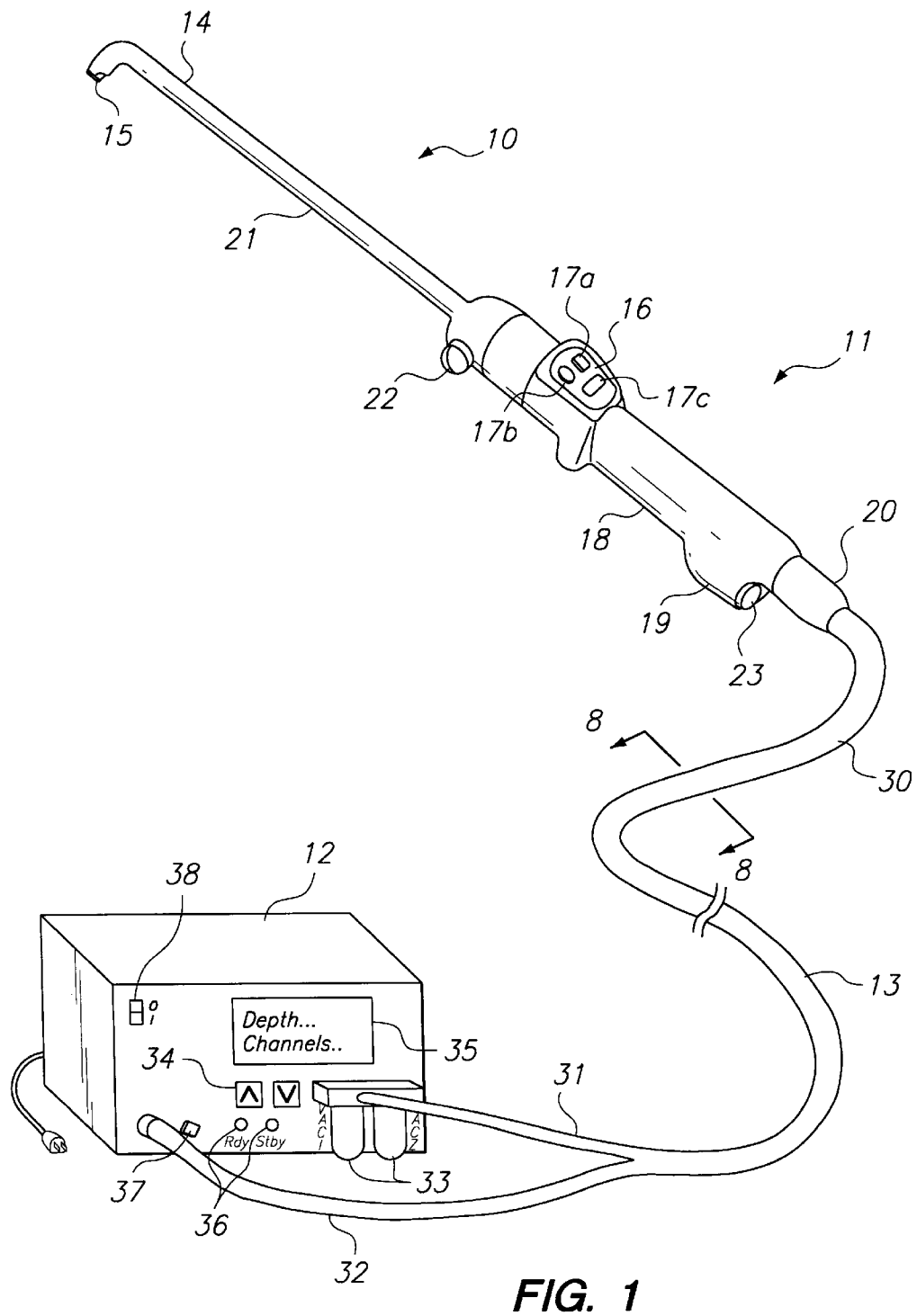
FIG. 1 is a perspective view of an illustrative embodiment of apparatus constructed in accordance with the present invention.

Referring to FIG. 1, illustrative apparatus 10 constructed in accordance with the present invention is described. Apparatus 10 includes handpiece 11 coupled to controller 12 via multi-lumen cable 13. Handpiece 11 includes end region 14 having cutting head 15 for forming transmural channels in an organ, such as the heart. Controller 12 houses the mechanisms that drive cutting head 15, as well as one or more vacuum sources that aspirate severed tissue from the operative site. Handpiece 11 and cable 13 preferably are pre-sterilized and discarded after a single use, while controller 12 is generally kept outside the sterile field and is reusable. Alternatively, only a portion of the handpiece, such as the elongated shaft and cutting head, described hereinafter, are disposable after a single use, while the body of the handpiece and cable are sterilizable for repeated use.

Handpiece 11 includes control panel 16 having buttons 17a–17c, body 18, tissue filter compartment 19, connector 20, elongated shaft 21 and articulation control means 22. As described in detail hereinafter, buttons 17a–17c on control panel 16 control actuation of apparatus 10. Body 18 serves as a hand grip that permits a clinician to manipulate the handpiece, while articulation control means 22 enables the clinician to articulate end region 14. Tissue filter compartment 19 is sealed by removable plug 23, and houses a filter that collects tissue aspirated from the operative site during the channel forming process.

Cable 13, which couples handpiece 11 to controller 12, includes distal end 30 and proximal ends 31 and 32. Proximal end 31 preferably includes two lumens, which connect, respectively, to high and low level suction vacuum pumps in controller 12. Proximal end 32 couples cutting head 15 and the electronic elements of handpiece 11, including control panel 16, to controller 12.

Controller 12, described in greater detail hereinafter, illustratively includes one or more vacuum sources coupled to traps 33, a coupling to accept proximal end 31 of cable 13, feature selection buttons 34, display panel 35, indicator lights 36, coupling and latch mechanism 37, and power switch 38. Controller 12 houses a power supply that powers the drive mechanisms, vacuum pumps, and electronics from standard 60 Hz AC current.

Referring now to FIGS. 1 and 2A–2C, the internal arrangement of an illustrative handpiece 11 constructed in accordance with the present invention is described. Body 18, which may be cast from a high strength plastic or metal alloy, includes compartment 40 that houses control panel 16, wiring lumen 41, low level suction lumen 42 and chamber 43. Chamber 43 is preferably a circular bore, and communicates with high level suction port 44 and drive cable lumen 45. Tissue filter compartment 19 communicates with high level suction port 44, suction port 46, and outlet 47. Plug 23 is removably engaged with outlet 47 of tissue filter compartment 19, so that tissue filter 48 may be periodically replaced during a procedure. Chamber 43 also preferably includes a bore 49 in which position sensor 50, illustratively a Hall effect sensor, is disposed, with the wires from sensor 50 routed from bore 49 through compartment 40 and wiring lumen 41.

Elongated shaft 21 is coupled to distal end of body 18, and comprises rigid proximal portion 55, articulation region 57 and stabilization means 58. Bore 59 runs the length of elongated shaft 21. In FIG. 2A, stabilization means 58 includes suction cup 60 having bore 61 that communicates with the distal end of bore 59 of elongated shaft 21. The proximal end of bore 59 opens into chamber 62 formed in the distal endface of body 18. Rigid portion 55 of elongated shaft 21 preferably comprises a relatively rigid material, such as stainless steel.

Articulation region 57 preferably comprises soft and flexible material 63, such as silicone, which is coated onto helical wire coil 64, for example, by sintering. In FIG. 2B, articulation region 57 is shown comprising helical wire 64 captured between inner layer 63a and outer layer 63b of flexible material 63. Tendon 65 is connected at one end to stabilization means 58 and at the other to axle 66 of articulation control means 22, illustratively thumb wheel 67. When thumbwheel 67 is rotated in a counterclockwise direction, tendon 65 causes stabilization means 58 to deflect from the longitudinal axis of the elongated shaft, as depicted in FIG. 1. Applicant expects this feature to be particularly advantageous in articulating end region 14 to permit access to posterior or otherwise hard-to-reach regions of the left ventricle.

Referring now to FIGS. 2A–2C, 3 and 4, cutting head 15 and its associated drive train are described. Cutting head 15 comprises tube 70 having sharpened distal end 71 and bore 72. Tube 70 is affixed to drive coupling 56, which in turn is disposed for reciprocatory and rotary motion in a portion of stabilization means 58 forming bushing 73. Specifically, cutting head 15, formed of tube 70 and the distal end of drive coupling 56, may be extended beyond distal endface 74 of stabilization means 58 by approximately 40 mm, while rotating at speeds of 50–50,000 RPM. Tube 70 preferably comprises a rigid biocompatible material, such as stainless steel, having a wall thickness of 0.002 to 0.005 inches, and a length of about 0.1–0.5 inches. Tube 79 may be affixed to drive coupling 56 by any suitable means, including welding or soldering, and preferably includes filets 70a, e.g., formed of solder, which provide a gradual taper between the exterior of tube 70 and drive coupling 56.

Drive coupling 56 is connected at its proximal end to drive tube 76, for example, by welding. Drive coupling 56, as best shown in FIG. 2B, preferably comprises a counterwound helical coil having inner coil 56a wound in a first direction and covered by outer coil 56b wound in an opposite direction. Drive coupling 56 is in turn enclosed within guide sheath 75. As shown in FIG. 4, guide sheath 75 preferably comprises a tight pitch helical coil 77 or tubular metal mesh covered with soft elastomer 78, such as polytetrafluoroethylene (PTFE). Alternatively, guide sheath 75 may comprise a tube of a flexible polymer, such as polyethylene.

Drive coupling 56 has central lumen 79 that communicates with bore 72 of tube 70 at its distal end and bore 80 of drive tube 76 at its proximal end. Coupling 56 transmits rotational and linear motion of drive tube 76 to cutting head 15, while guide sheath 75 maintains a high level of suction in lumen 79, even when articulation of articulation region 57 causes the flexible coupling to assume an angled shape, e.g., up to a 180° angle.

Drive tube 76 is coupled at its proximal end to spool 81. As shown in FIG. 3, spool 81 comprises tube 82 having closed distal face 83, frustoconical portion 81 formed by struts 84, and hub 85. Distal face 83 includes central aperture 86 and a flange (not shown) that accepts the proximal end of drive tube 76. Hub 85 couples spool 81 to drive cable 87. Drive cable 87 extends to proximal end 32 of cable 13. Tube 82 includes two regions 88 of magnetic material disposed in evenly spaced-apart relation around its circumference. Spool 81 is enclosed within chamber 43 of body 18 so that it may rotate and translate in the longitudinal direction within chamber 43 responsive to force and torque applied by drive cable 87. Spool 81 also may include wiper seal 82a comprising, for example, an elastomeric flange, to wipe tissue from the interior diameter of chamber 43 and prevent its buildup in the path of travel of spool 81. Seal 82a may, in addition, assist in maintaining the high level of suction in chamber 43.

Drive tube 76 is disposed through bushing 89. Bushing 89 in turn is disposed in plug 90, which is seated in the distal end of chamber 43. Plug 90 preferably is installed during the manufacturing process, after spool 81 (already connected to drive cable 87 and drive tube 76) is disposed in chamber 43. Drive cable 87 is also disposed through bushing 91, which is seated in recess 92 in drive cable lumen 45.

With reference now to FIGS. 2A and 3, a high level suction is drawn through suction port 47, tissue filter compartment 19, high level suction port 44, and chamber 43, where it is communicated to bore 80 of drive tube 76 through aperture 86 of spool 81. When cutting head 15 is advanced into a target tissue, responsive to distal displacement of spool 81 in chamber 43 by drive cable 87, tissue is severed by sharpened end 71 of cutting head 15. That tissue is aspirated through bores 72, 79 and 80 into the interior of spool 81. The tissue then exits spool 81 through the spaces between struts 84, and is drawn into tissue filter 48. The path of the aspirated tissue is shown by arrows A in FIG. 3. Tissue filter 48 preferably comprises a replaceable light-weight membrane or mesh, e.g., formed from paper or a polymer mesh or screen.

Regions 88 of magnetic material on spool 81, in connection with Hall effect sensor 50, provide two safety functions that enable controller 12 to monitor operation of handpiece 11. Preferably, sensor 50 generates a signal only when the magnetic material on spool 81 is aligned with the sensor, for example, when the spool is in its proximal-most position. Thus, regions 88 and sensor 50 enable controller 12 to determine the location of the spool within chamber 43, for example, to ensure that the cutting head has fully retracted after a boring a channel in tissue. In addition, the presence of magnetic regions 88 enables controller 12 to determine that spool 81 is rotating within chamber 43 by detecting periodic fluctuations in the output of sensor 50. In particular, the frequency of the signal output by sensor 50 should be directly proportional to the rotational speed of spool 81 within chamber 43. As will be apparent to one of skill in the machine design, sensors of other types may be advantageously employed to provide positional information in place of Hall effect sensor 50 and magnetic regions 88.

Referring now to FIGS. 5A and 5B, end region 14 of elongated shaft 21 is described in greater detail. Stabilization means 58 illustratively comprises suction cup 60 in distal endface 74, and beveled portion 95. In FIG. 5A, tube 70 of cutting head 15 is shown slightly extended from distal endface 74 of the stabilization means. In one preferred embodiment, stabilization means 58 comprises a transparent material, such as silicone, polyurethane, polyethylene, polypropylene or polycarbonate, so that the path of cutting head 15 is visible. Bushing 73 of stabilization means 58 also preferably comprises a layer of low frictional material, e.g., polytetrafluoroethylene (teflon), to support cutting head 15.

With respect to FIG. 6, the internal arrangement of the components of controller 12 is described. Controller 12 comprises housing 100 containing vacuum equipment compartment 101 separated by environmental wall 102 from drive assembly and electronics compartment 103. Vacuum equipment compartment 101 preferably contains high level vacuum pump 104 and low level vacuum pump 105. High level vacuum pump 104 preferably creates a high level of suction, e.g., between about 400–800 mm Hg, and preferably about 730 mm Hg, while low level vacuum pump creates a lower level of suction, e.g., less than 400 mm Hg and preferably, about 250 mm Hg.

Vacuum pumps 104 and 105 are coupled to traps 33 via coupling 106, which are in turn coupled to proximal end 31 of cable 13 via coupling 107. The inlet line for each vacuum pump includes flow sensor 108 and pressure sensor 109. Control electronics 110 monitors the outputs of sensors 108 and 109 to ensure that apparatus 10 is functioning properly, e.g., to ensure that there are no excursions indicating a blocked line.

In a preferred embodiment of the invention, in which cutting head 15 is configured for rotary motion as well as longitudinal displacement, drive assembly and electronics compartment 103 houses control electronics 110, e.g., a suitably programmed microprocessor or analog circuitry, power supply 111, linear motor 112, rotary motor 113, drive tube 114, display panel 35, indicator lights 36, coupling and latch mechanism 37, and power switch 38. Linear motor 112, which may be either a linear stepper motor or a rotary motor coupled to a lead screw arrangement, is connected to drive tube 114 by coupling 115, and causes drive tube 114 to be reciprocated with respect to the longitudinal axis of drive tube 114. When this motion is translated through drive cable 87, it causes cutting head 15 to extend and retract beyond distal endface 74 of stabilization means 58 (see FIG. 2A).

Rotary motor 113 is coupled to drive tube 114 by right angle gearing 116. Drive tube 114 preferably includes a D-shaped outer diameter, so that a gear of right angle gearing 116 having a mating key slot continuously transmits torque to drive tube 114 even while it is being extended or retracted by linear motor 112. Motors 112 and 113 are each coupled to control electronics 110, which activates the motors responsive to signals generated by the buttons of control panel 16 on handpiece 11.

Indicator lights 36 preferably provide information concerning the state of the apparatus. For example, one of the lights 36 may become illuminated to indicate that the cutting head is ready to be activated, while the other indicates that the apparatus is in a standby mode. Display panel 35 also may display information concerning the state of the apparatus, such as the instantaneous suction levels, flow rates and error messages, as well as, for example, provide information regarding the rotational speed of the cutting head, and the number and depth of channels formed.

Figure 7A:
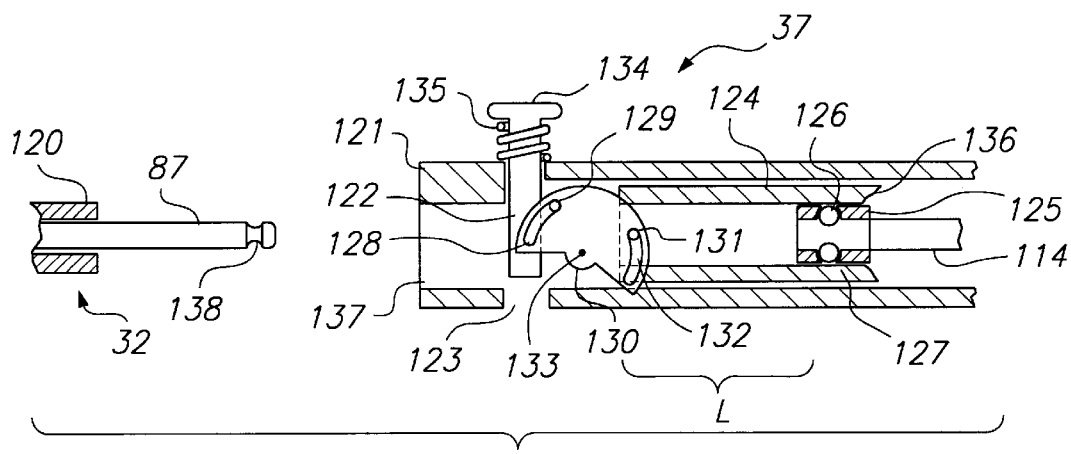
FIGS. 7A and 7B are, respectively, side sectional and end views of a coupling and latch mechanism for interconnecting the cable to the controller.
Figure 7B:
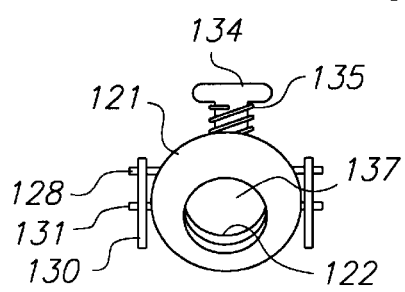

Referring to FIGS. 7A and 7B, an illustrative embodiment of coupling and latch mechanism 37 is described. Mechanism 37 is configured to engage outer sheath 120 of proximal end 32 of cable 13 in a stationary manner, while enabling drive cable 87 to engage drive tube 114 for reciprocatory and rotary motion.

Mechanism 37 comprises housing 121 having hoop 122 disposed in slot 123 for sliding movement, and sleeve 124 disposed on ring 125. Ring 125 includes balls 126 captured in bores 127, and is affixed to the distal end of drive tube 114. Hoop 122 has pivot pins 128 engaged in slots 129 of cams 130, while sleeve 124 has pivot pins 131 engaged in slots 132 of cams 130. In addition, cams 130 are fixed to pivot on pins 133. Hoop 122 includes button 134 and spring 135 that biases the hoop 122 in a retracted position in slot 123. Sleeve 124 has chamfer 136 along the interior of its proximal end, so that when sleeve 124 is in its relaxed position, balls 126 project into the interior of ring 125.

Operation of mechanism 37 is as follows: when it is desired to connect proximal end 32 of cable 13 to controller 12, drive tube 114 and ring 125 are moved to the proximalmost position in sleeve 124. The clinician then depresses button 134 against the bias of spring 135. This causes hoop 122 to move downward in slot 123, so that the opening in hoop 122 is aligned with opening 137 of housing 121. Downward movement of hoop 122 also causes pins 128 to ride downward in slot 129, thereby causing cams 130 to rotate (e.g., counterclockwise in FIG. 7A). As cams 130 rotate, slots 132 exert a force on pivot pins 131 which draw sleeve 124 towards hoop 122. This movement of sleeve 124 releases balls 126 in ring 125.

Proximal end 32 of cable 13 is then inserted in mechanism 37. In particular, the proximal end of drive cable 87 is inserted into ring 125 until balls 126 enter detent 138 in the drive cable. In addition, the proximal end of outer sheath 120 also extends into the opening in hoop 122. When the force on button 134 is released, spring 135 causes hoop 122 to engage outer sheath 120 of the cable 13, thus locking the outer sheath in place. Simultaneously, upward movement of hoop 122 causes cams 130 to rotate sufficiently for sleeve 124 to be urged by pivot pin 131 away from hoop 122. This motion causes sleeve 124 to retain balls 126 in detent 138 of drive cable 87. As will of course be apparent to one of skill in machine design, to ensure that sleeve 124 retains balls 126 within detent 138, sleeve 124 preferably should have a length L sufficient to accommodate the full stroke of drive tube 114.

Figure 8:
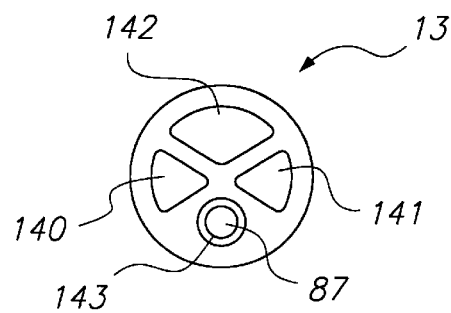
FIG. 8 is a sectional view of the cable of the apparatus of FIG. 1, taken along view line 8—8 of FIG. 1.

With respect to FIG. 8, the configuration of cable 13 along the section indicated by view lines 8—8 in FIG. 1 is described. Cable 13 is preferably sufficiently long, e.g., approximately 1 to 1.5 m long, for controller 12 to be placed outside the sterile field during operation of apparatus 10. Cable 13 comprises a flexible material, such as polyethylene, which is extruded to form lumens 140–143. Alternatively, each of lumens 140–143 may be separately formed and then bonded together or enclosed within a common sheath, such as a heat shrinkable sheath. Illustratively, lumen 140 is coupled to low level suction lumen 42 of handpiece 11, lumen 141 is coupled to suction port 47 of handpiece 11, lumen 142 is used for routing electrical wires between handpiece 11 and controller 12, and lumen 143 houses drive cable 87. Lumen 143 may be lined with a lubricious material, such as PTFE, to reduce friction between drive cable 87 and the walls of the lumen.

Referring again to FIGS. 1, 2 and 6, operation of apparatus 10 of the present invention is described. As initial set-up for the procedure, proximal ends 31 and 32 of cable 13 (which are already coupled to handpiece 11) are coupled to controller 12, and power switch 38 is turned on. Controller 12 may then be programmed via feature selection buttons 34, or a keyboard (not shown), for example, to select the depth of the transmural channels to be cut and the parameters displayed on display panel 35.

In accordance with known surgical methods for performing TMR, a portion of the patient's left ventricle is exposed by thorocotomy or through apertures opened between the patient's ribs. The clinician first depresses button 17a to "arm" the handpiece, which signals controller 12 to activate vacuum pumps 104 and 105, and activate rotary motor 113 to rotate drive tube 114. This rotation is transmitted from drive cable 87 to spool 81, and then through drive tube 76 and drive coupling 56 to cutting head 15. The clinician then manipulates handpiece 11 to bring distal endface 74 of stabilization means 58 into contact with the epicardium in the vicinity of the left ventricle, either with or without articulation of end region 14, as required by the access conditions of the operative site.

Once stabilization means 58 is in a desired position over a target tissue, button 17c on control panel 16 is actuated to cause vacuum pump 105 to draw low level suction through lumen 140, lumen 42, chamber 62, bore 59 and suction cup 60 to engage the target tissue. For this purpose, controller 12 may include, for example, a gate valve in coupler 106 that rotates responsive to control electronics 110 and the signal from button 17c to alternate between a bleed port and the connection to lumen 140. In this manner, low-level suction may be selectively provided through suction cup 60 responsive to actuation of button 17c.

After distal end 14 of handpiece 11 is engaged with the target tissue, the clinician actuates button 17b to initiate the transmural cutting process. Specifically, when button 17b is depressed, control electronics 110 activates linear motor 112 to cause drive tube 114 to extend and retract with a preselected velocity profile input. This longitudinal movement of drive tube 114 is transmitted via drive cable 87 to cutting head 15, which extends through the ventricle wall and then retracts. Simultaneous with this longitudinal motion, cutting head 15 is rotated at high speed and high level suction is drawn through bore 72 of the cutting head to aspirate severed tissue.

Tissue aspirated from the target site is drawn through drive coupling 56 and drive tube 76 and exits into the interior of spool 81, from which it is drawn through chamber 43 into tissue filter 48. Because high level vacuum pump 104 includes in-line flow and pressure sensors 108 and 109, controller 12 may alert the clinician when the suction through cutting head 15 has dropped, for example, due to filling of tissue filter 48. The clinician may then, between channel forming steps, remove plug 23 and replace tissue filter 48 with a clean filter.

Applicant expects that extension and retraction of cutting head 15 may be readily accomplished during diastole of a single cardiac cycle (i.e., within about one-tenth to one-half of a second). In addition, however, it is believed that if the tissue cutting process is extended over several beats of the heart, it may be advantageous to initiate the cutting process (i.e., activate button 17b) when the heart is in diastole. In this case, the output of an EKG monitor may be used by the clinician to time initiation of the tissue cutting process with the onset of diastole.

When the cutting process for a target site is complete, the clinician depresses button 17c to cease low level suction through suction cup 60, thereby disengaging stabilization means 58 from the tissue. It has been observed that the outlet of the transmural channel will clot off in a few minutes, leaving a channel through which blood from the left ventricle may perfuse the myocardium. The clinician then repositions the cutting head to an adjacent region of the epicardium, including adjusting the degree of articulation of end-region 14, and repeats the process.

Of course, care must be taken in repositioning the end region so that suction cup 60 is not positioned over a previously formed channel, so as to avoid having the suction drawn through suction cup 60 draw blood through the previously formed channel.

Applicant expects that 20 to 50 transmural channels, each about 1 mm to 5 mm in diameter, may be formed in the heart in about fifteen minutes or less, and will provide improved myocardial perfusion. Advantageously, articulation control means 22 enables the degree of articulation of end-region 14 to be adjusted in situ and as required to obtain access for the selected area to be treated. As described hereinbelow with respect to FIG. 13, handpiece 11 may include a fiber optic cable for viewing the target site and angulation of the end-region in such regions.

Figure 9A:
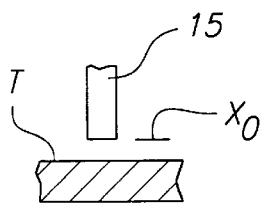
FIGS. 9A to 9E and 9F are, respectively, side views of the cutting head of FIG. 2 as it penetrates a thickness of tissue, and a graph showing the linear speed of the cutting head as a function of displacement.
Figure 9B:
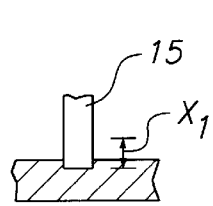
Figure 9C:
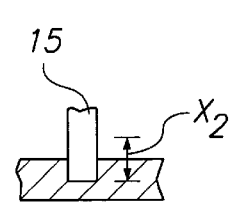
Figure 9D:
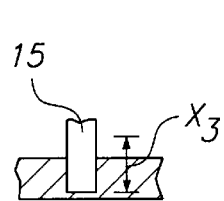
Figure 9E:
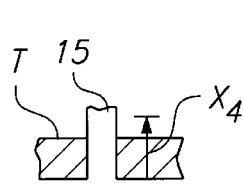
Figure 9F:
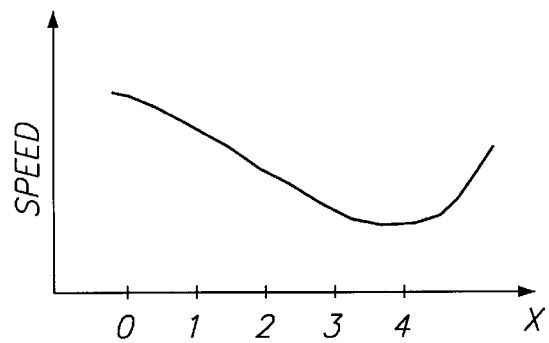

Referring now to FIGS. 9A to 9F, a speed control feature of a preferred embodiment of the present invention is described. In FIGS. 9A to 9E, the position of cutting head 15 at a series of consecutive displacements $X_0$–$X_4$ is shown during the process of forming a transmural channel in tissue T. FIG. 9F depicts the speed of the cutting head at each of the displacements illustrated in FIGS. 9A to 9E.

In accordance with one aspect of the present invention, the linear speed of cutting head 15 varies in accordance with the depth of penetration of the cutting head into tissue T. As shown in FIGS. 9C and 9D, as the cutting head nears the inner surface of the tissue wall (near completion of the channel formation), the speed of the cutting head is reduced to provide adequate time for the high level suction to aspirate severed material. In this manner, the potential for ejecting severed material into the organ from the distal surface of the tissue is reduced, and thus the risk of embolization is reduced. After the cutting head has completely penetrated the tissue wall, the cutting head is rapidly retracted.

To implement this feature, control electronics 110 may be programmed to control the speed at which linear motor 112 reciprocates drive tube 114 to provide a speed profile such as described above with respect to FIG. 9F. Control electronics 110 may in addition employ additional positional information generated by an extended position sensing element (not shown) similar to Hall effect sensor 50 to more accurately control the speed profile. In addition, control electronics 110 may also employ the signal generated by pressure sensor 109 to determine when the cutting head has completely penetrated the tissue.

With respect to FIG. 10, an alternative embodiment of the stabilization means of the present invention is described. Stabilization means 150 includes suction cup 151, bore 152 for the cutting head, and light source 153, e.g., a light emitting diode (LED) or laser diode, disposed in the transparent material forming stabilization means 150. Light source 153 is connected to a suitable power supply by lead wires 154 and 155. When a voltage is supplied across lead wires 154 and 155, light source 153 emits light that exits the distal end face of the stabilization means in an approximately annular illumination beam to form illumination spot 156. Applicant expects that illumination spot 156 may be advantageously used to position the stabilization means 150 on the tissue so that suction cup 151 does not overlap a site at which a transmural channel had been previously formed.

Alternatively, shaft 21 may include a spring-loaded retractable stylet (not shown) that indicates the position of the suction cup before the suction cup is engaged to the tissue.

Referring now to FIGS. 11A and 11B, further alternative embodiments of stabilization means constructed in accordance with the present invention are described. In FIG. 11A, stabilization means 160 is similar in design to that of FIG. 5A, except that beveled surface 95 is replace with fixed tube 161 having beveled sharpened tip 162 and lumen 163. The bevel of tip 162 renders the tip non-coring, so that when the beveled end of tube 161 is inserted into the tissue, a flap of tissue is cut and folded back, rather than severed. The cutting head in this embodiment is reciprocated through lumen 163, and otherwise operates as described hereinabove. Applicant expects that use of beveled tube 161 will accelerate the process of clotting of the transmural channel on the epicardium, by reducing the amount of tissue removed from outer thickness of the tissue wall, and leaving a slit instead of a cored cut channel at the surface.

In FIG. 11B, an alternative embodiment of the stabilization means of FIG. 11A is shown, in which beveled tip 164 of tube 165 is disposed flush with, or slightly recessed from, distal endface 166 of stabilization means 167. In this embodiment, beveled tip 164 does not pierce the surface of the tissue until the high level suction draws the tissue inwards through opening 168. It is expected that the embodiment of FIG. 11B will provide the same advantage as the embodiment of FIG. 11A, i.e., less outer wall tissue removal and faster hemostasis, but with a lower risk of inadvertently piercing or tearing the tissue while repositioning the distal end of the device.

In FIGS. 12A to 12F, different modalities of operation of a cutting head constructed in accordance with the present invention are described. In FIGS. 12A–12F, various cutting heads are described as illustratively constructed from a sharpened tubular member, similar to that described with respect to FIG. 2A. All of the embodiments of FIGS. 12A to 12E described hereinbelow preferably include a central lumen that may be coupled to a vacuum source for aspirating tissue severed by the cutting head from the treatment site, thus reducing the risk of embolization.

In FIG. 12A, cutting head 170 is arranged for rotary and longitudinal motion, like cutting head 15 described hereinabove. In FIG. 12B, cutting head 172 is arranged for rapid reciprocation in the distal and proximal directions, which motion is superimposed on the distal and proximal motion of the cutting head caused by actuation of the linear motor 112. In FIG. 12C, cutting head 174 is reciprocated rapidly in the longitudinal direction while experiencing rapidly alternating angular motion of several degrees, for example, 90 to 120 degrees, which motion is again superimposed on the overall distal and proximal motion caused by linear motor 112.

In FIG. 12D, cutting head 176 is vibrated at high frequency, either in the longitudinal direction, an angular direction, or both, to cause emulsification of the tissue contacted by the cutting head. Vibration of cutting head 176 may be accomplished either by a mechanical gear driven arrangement, or may be provided by an ultrasonic device. In either case, the vibratory motion of the cutting head is in addition to motion in the distal and proximal directions caused by actuation of linear motor 112.

In FIG. 12E, cutting head 178 is described together with actuator 180. Cutting head 178 is advanced at very high speed in the distal direction, for example, by a hydraulic actuator, to pierce the heart tissue in a single motion. In this embodiment, drive tube 76 need not be rotated, and linear motor 112 of controller 12 is replaced by actuator 180 comprising piston 181 that reciprocates within cylinder 182, valving 183 that selectively couples piston 181 to source of high pressure 184 (e.g., a cylinder of pressurized gas) and a source of low pressure 185 (e.g., a vacuum source).

In FIG. 12F, a yet further alterative embodiment of a cutting head constructed in accordance with the present invention is described. Cutting head 190 comprises a nozzle through which fluid, for example, saline, is ejected at high pressure, for example 1000 psi. The fluid stream impinges upon and cuts a channel in the tissue. In this embodiment, drive tube 76 remains stationary and motors 112 and 113 are replaced by a high pressure hydraulic pump 192.

Figures 13A, 13B:
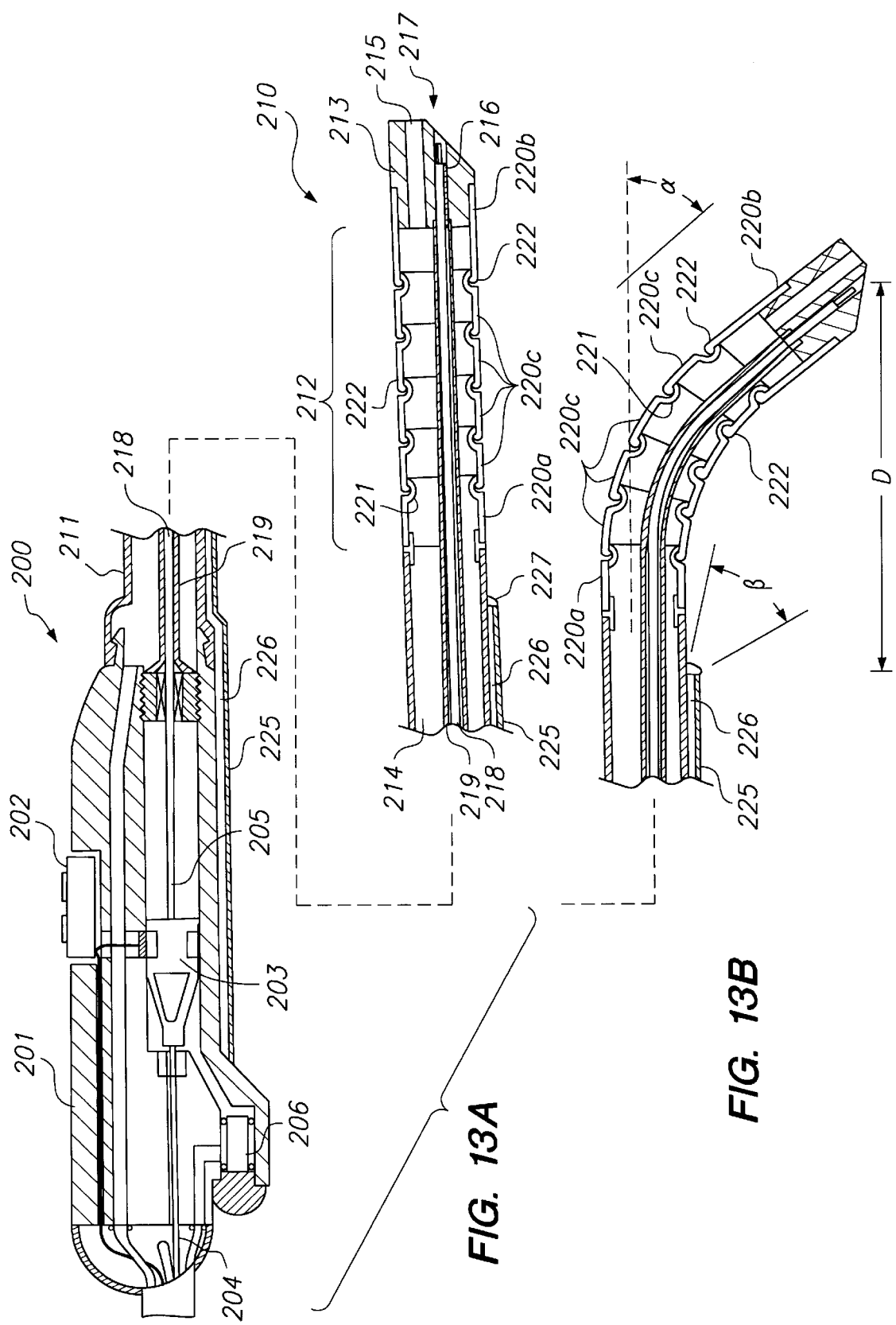
FIGS. 13A and 13B are side sectional views of the handpiece of the present invention having an alternative embodiment of the articulation mechanism constructed in accordance with the present invention.

Referring now to FIG. 13A, an alternative embodiment of the handpiece of the present invention is described, wherein the articulation region comprises a bendable series of interconnect rigid segments, rather than an flexible material as described with respect to FIG. 2A. Handpiece 200 comprises body 201 configured as described above with respect to body 18 of FIG. 2A, and houses control panel 202, spool 203, drive cable 204, drive tube 205 and tissue filter 206, all as described above with respect to like parts of FIG. 2A.

Elongated shaft 210 is coupled to the distal end of body 201, and comprises rigid proximal portion 211, articulation region 212 and stabilization means 213. Bore 214 runs the length of elongated shaft 210. Stabilization means 213 comprises suction cup 215 and bushing 216 in which cutting head 217 rotates and reciprocates, as described hereinabove with respect to like parts in FIG. 2A. Drive tube 205 is coupled to cutting head 217 by drive coupling 218, as described above with respect to FIGS. 2A and 2B. Alternatively, drive tube 205 may be omitted, with drive coupling 218 being connected directly to spool 203. Drive coupling 218 is enclosed within guide sheath 219.

In the embodiment of FIGS. 13, articulation region 212 comprises a plurality of interconnected segments 220. Segment 220a couples articulation region 212 to proximal region 211 and includes curved flange 221, while segment 220b couples the articulation region to stabilization means 213 and includes ridge 222. Each of segments 220c disposed between segments 220a and 220b includes both curved flange 221 at its distal end and ridge 222 at its proximal end. Each ridge 222 is slidingly captured on the curved flange of the next proximal segment. In this manner, each segment may be rotated slightly so that its longitudinal axis forms an angle with the longitudinal axis of the preceding segment.

As shown in FIG. 13B, when the deflections of the longitudinal axes of segments 220 are accumulated over several segments, stabilization means 213 may be positioned at an angle α, e.g., 45° or 90°, with respect to the longitudinal axis of proximal portion 211. In one embodiment, each ridge 222 is frictionally coupled to the preceding curved flange 221, so that segments 220 may be bent to a desired shape and will retain that shape until subsequently moved. For this embodiment, the clinician first adjusts the position of the cutting head, and then inserts elongated shaft 210 to reach the operative site. In an alternative embodiment, an articulation control mechanism and tendon (see elements 65 to 67 of FIG. 2A) may be provided to adjust the degree of angulation of articulation region 212 in-situ.

Still referring to FIG. 13, body 201 and elongated shaft 210 may in addition include lumen 225 containing fiber optic element 226. Fiber optic element 226 is coupled to lens 227 at its distal end, and to an imaging system (not shown), per se known, at its distal end. Accordingly, fiber optic element 226 may be used to view the target site, the degree of articulation of the end region of elongated shaft 210, and the operation of cutting head 217. Preferably lens 227 has a field of view β that encompasses the useful range of movement of stabilization means 213, e.g., about 15° to 60° from the longitudinal axis of shaft 210, depending upon the axial distance D from the stabilization means to the lens 227. This feature may be advantageously employed, for example, with handpiece 11 of FIG. 2A, to enable the clinician to view adjustments of the articulation of the stabilization means and cutting head in-situ without removing the end region from the operative site.

Figure 14:
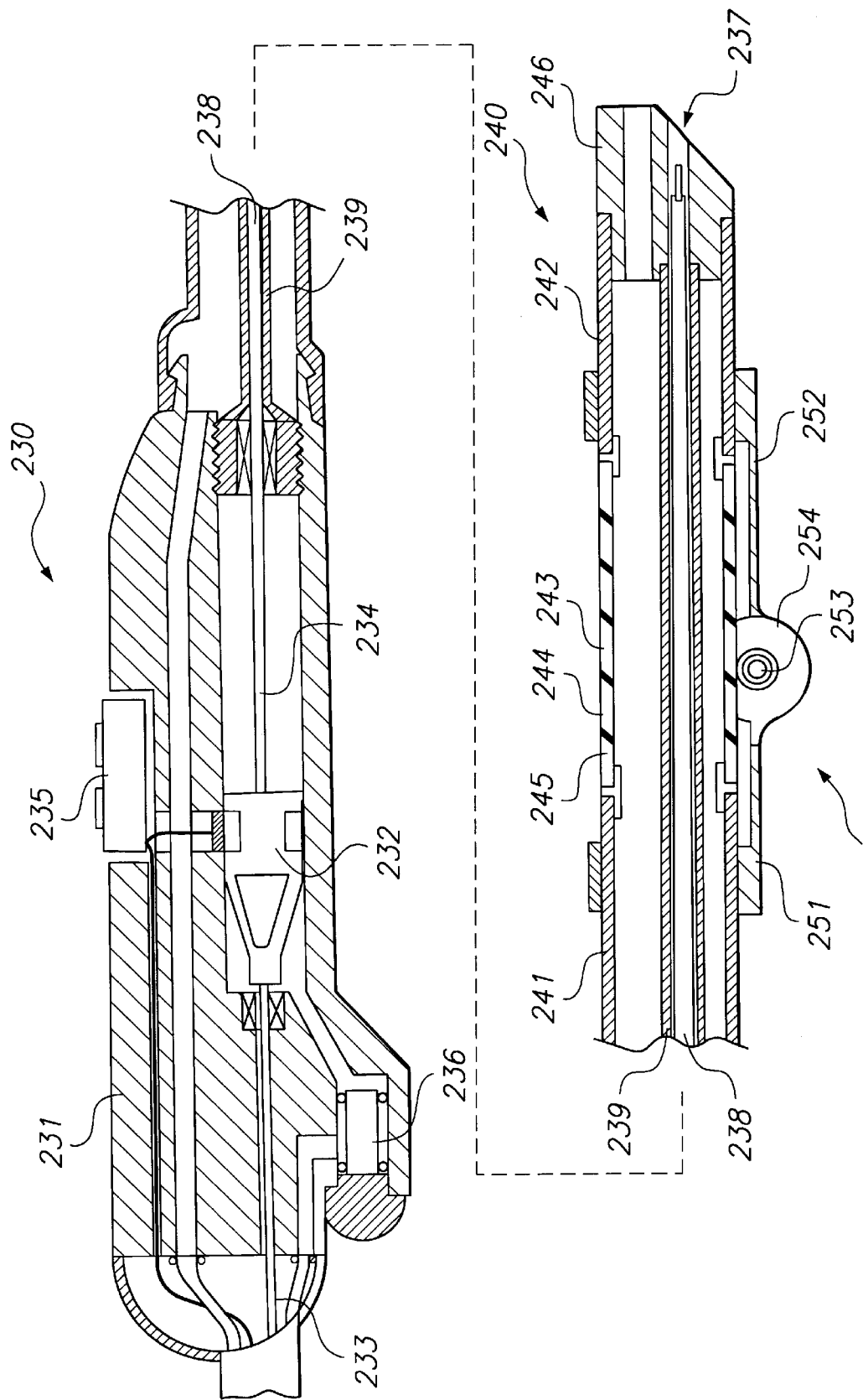
FIG. 14 is a side sectional view of the handpiece of the present invention having another alternative embodiment of the articulation mechanism.
Figure 15A:
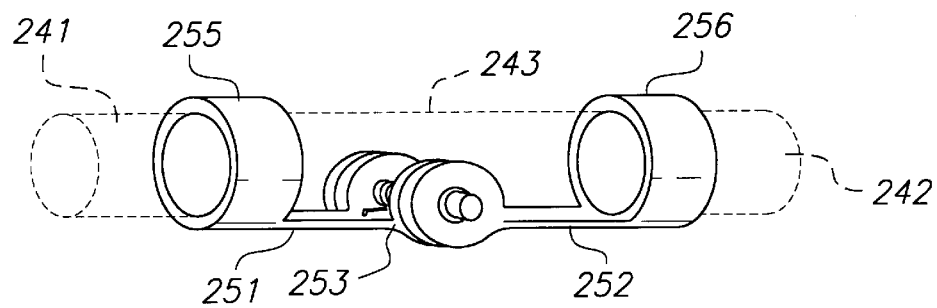
FIGS. 15A–15D are, respectively, perspective views in the straight and angled position, an exploded perspective view, and partial side view of an illustrative embodiment of the mechanism of FIG. 14.
Figure 15C:
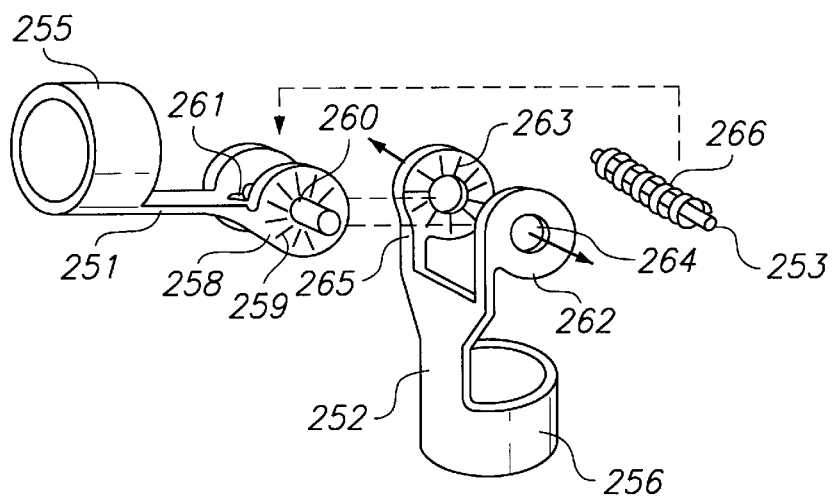
Figure 15D:
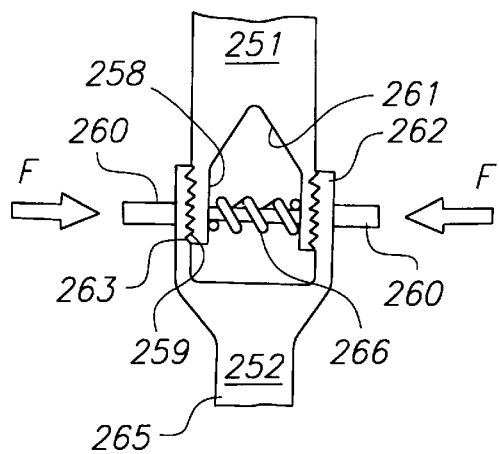
Figure 15B:
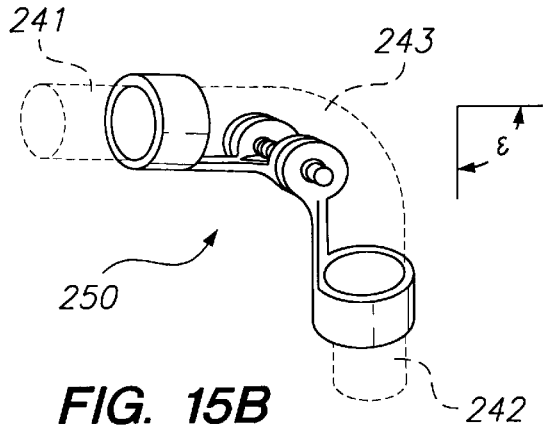
Figure 16A:
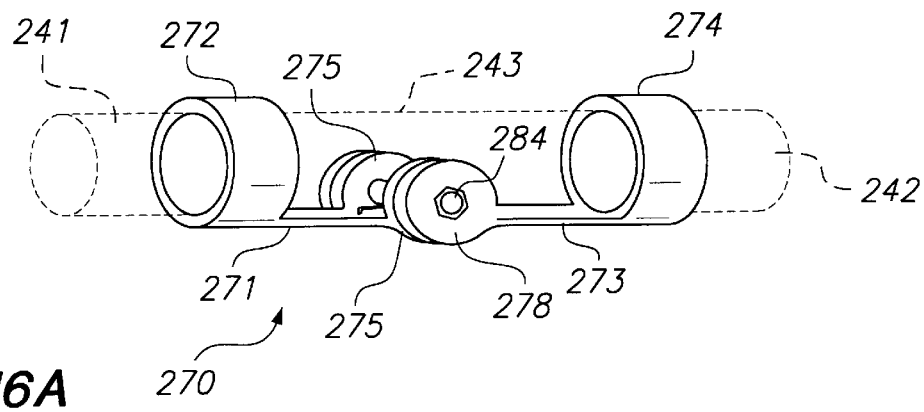
FIGS. 16A–16D are, respectively, perspective views in the straight and angled position, an exploded perspective view, and partial side view of an alternative embodiment of the mechanism of FIG. 14.
Figure 16C:
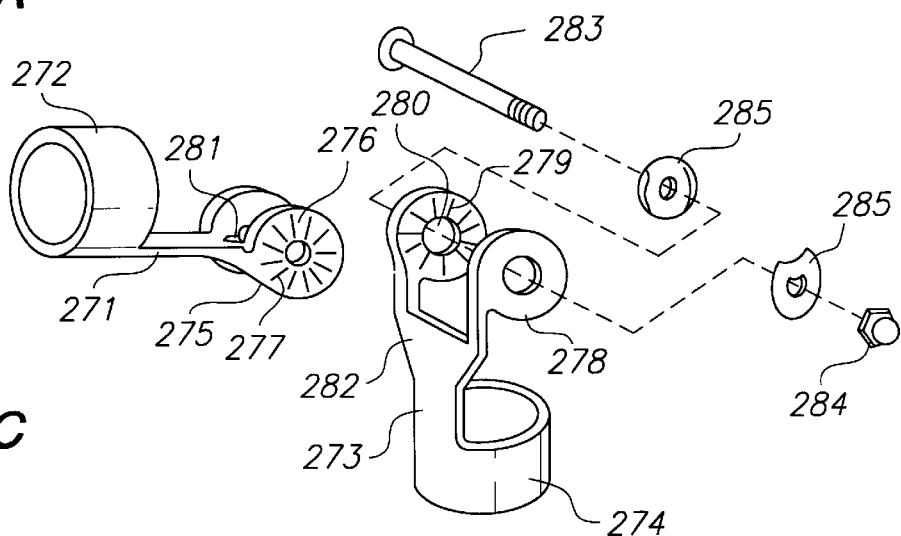
Figure 16D:
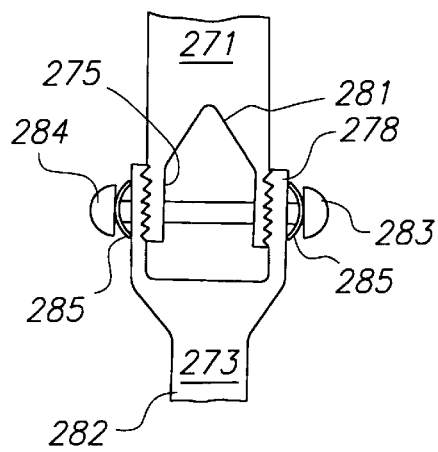
Figure 16B:
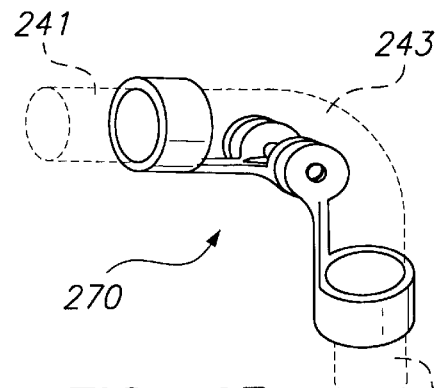

With respect to FIG. 14, another embodiment of the articulation region of the handpiece of the present invention is described. Handpiece 230 includes body 231 including spool 232, drive cable 233, drive tube 234, control panel 235, and tissue filter 236 as described hereinabove with respect to FIG. 2A. Cutting head 237 is coupled to drive tube 234 by drive coupling 238 enclosed in guide sheath 239, as described hereinabove with respect to previous embodiments. Elongated shaft 240 is coupled to the distal end of body 231, and includes rigid proximal and distal portions, 241 and 242, respectively, coupled to articulation region 243. Articulation region 243 preferably comprises helical coil 244 coated with elastomeric material 245, as described herein above with respect to FIG. 2A. Stabilization means 246 is coupled to the distal end of distal portion 242.

Handpiece 230 differs from handpiece 11 of FIG. 2A in that articulation control means 67 and tendon 65 are replaced with adjustable pivot assembly 250. Pivot assembly 250 includes hinged portions 251 and 252 coupled by pin 253. Each of hinged portions 251 and 252 is connected to proximal and distal portions 241 and 242, respectively, of elongated shaft 240. In accordance with this aspect of the invention, joint 254 formed by hinged portions 251, 252 and pin 253 may be adjusted to a desired angle, and holds the selected shape until subsequently readjusted. Articulation region 243 bends to conform to the shape imposed by pivot assembly 250. In this manner, a clinician may manually adjust the cutting head to a desired angle, for example, to access hard-to-reach portions of the anatomy, and then position the end-region in the operative site to form transmural channels. Specific embodiments of adjustable pivot assembly 250 are described below with respect to FIGS. 15 and 16.

Referring now to FIGS. 15A–D, pivot assembly 250 is described, wherein elongated shaft 240 is shown in outline for clarity. Hinged portion 251 includes tubular member 255, which engages proximal portion 241, while hinged portion 252 includes tubular member 256 which engages distal portion 242. Alternatively, hinged portions 251 and 252 may omit tubular members 255 and 256, and instead be affixed directly to the rigid portions of the shaft 240, e.g., by welding.

Hinged portion 251 includes washers 258 having grooves 259 and buttons 260. Washers 258 are disposed from the distal end of hinged portion 251 to form yoke 261. Hinged portion 252 includes washers 262 having ribs 263 disposed about apertures 264 to form yoke 265. When assembled, yoke 261 of hinged portion 251 is disposed within yoke 265, so that buttons 260 extend through apertures 264 and grooves 259 and ribs 263 are arranged in opposing relation. Spring 266 is disposed about pin 253, which in turn is slidingly engaged in bores (not shown) within buttons 261.

When assembled, spring 266 applies a compressive load on washers 258 that urges them against washers 262. This force compresses the washers together and urges grooves 259 and ribs 263 to intermesh, thus preventing rotation of one hinged portion relative to the other. By depressing buttons 260 as illustrated by arrows F in FIG. 15D, spring 266 may be compressed against its bias, and hinged portion 252 may be rotated relative to hinged portion 251, so that distal portion 242 of elongated shaft 240 forms an angle ε with respect to the longitudinal axis of proximal portion 241 of the shaft. Once the clinician has articulated the cutting head to a desired angle, buttons 260 are released, thereby causing grooves 259 and ribs 263 to again intermesh and lock the hinged portions into position.

With respect to FIGS. 16A–D, an alternative structure for adjustable pivot assembly 250 of FIG. 14 is described. Pivot assembly 270 is similar in construction to pivot assembly 250 of FIGS. 15. Hinged portion 271 is coupled to proximal portion 241 of elongated shaft 240 by tubular member 272, while hinged portion 273 is coupled to distal portion 242 by tubular member 274. Hinged portion 271 includes washers 275 having grooves 276 and apertures 277. Hinged portion 273 includes washers 278 having ribs 279 disposed around apertures 280. Washers 275 are disposed from the distal end of hinged portion 271 to form yoke 281, while washers 278 form yoke 282 on hinged portion 273. When assembled, yoke 281 of hinged portion 271 is disposed within yoke 282, so that grooves 277 and ribs 279 are arranged in opposing relation. Pin 283 is disposed through apertures 277 and 280 and engaged with nut 284, and captures concave lock washers 285 against the exterior surfaces of washers 278.

When assembled, lock washers 284 apply a compressive load on washers 278 that urges them against washers 275. This force compresses the washers together and urges grooves 277 and ribs 279 to intermesh, thus preventing rotation of one hinged portion relative to the other. The concave shape of lock washers 285 enable ribs 279 to slide or ratchet pass grooves 277 when a sufficiently high bending force is manually applied to hinged portions 271 and 273. Thus, the clinician may manually rotate hinged portion 271 relative to hinged portion 273 so that distal portion 242 of elongated shaft 240 forms an angle with respect to the longitudinal axis of proximal portion 241 of the shaft. Once the clinician has articulated the cutting head to a desired angle, grooves 277 and ribs 279 again intermesh and lock the hinged portions into position.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for use with a first vacuum source to form a channel in tissue, the apparatus comprising:
    a handpiece having:
        a body,
        a shaft coupled to the body, the shaft having a lumen, a longitudinal axis and an articulation region;
        a cutting head having a bore coupled to the first vacuum source, a first position wherein the cutting head extends from within the lumen to form a channel in the tissue, tissue severed by the cutting head being aspirated through the bore by the first vacuum source, and a second position wherein the cutting head is retracted within the lumen; and
        means for articulating the articulation region to dispose the cutting head at an angle relative to the longitudinal axis of the shaft.

2. The apparatus as defined in claim 1 wherein the apparatus further comprises:
    a controller housing a linear motor; and
    a cable coupling the linear motor to the cutting head to move the cutting head between the first and second positions.

3. The apparatus as defined in claim 1 wherein the first vacuum source is housed within the controller.

4. The apparatus as defined in claim 1 further comprising a rotary motor disposed within the controller and coupled by the cable to the cutting head to rotate the cutting head.

5. The apparatus as defined in claim 4 wherein the handpiece further comprises a control panel having buttons that cause activation of the linear and rotary motors.

6. The apparatus as defined in claim 4 wherein the cable comprises a drive cable and the apparatus further comprises a coupling that transmits rotary motion and longitudinal motion from the rotary and linear motors, respectively, to the drive cable.

7. The apparatus as defined in claim 6 wherein the handpiece further comprises a spool coupled between the drive cable and the cutting head, the spool including struts defining apertures that permit tissue aspirated through the bore of the cutting head to pass to a tissue filter.

8. The apparatus as defined in claim 1 wherein the cutting head, in the first position, also experiences motion selected from the group consisting of reciprocatory motion, angular motion or vibrational motion.

9. The apparatus as defined in claim 1 wherein the apparatus further comprises means for stabilizing the cutting head in contact with the tissue.

10. The apparatus as defined in claim 9 wherein the means for stabilizing comprises a suction cup disposed on the shaft near the cutting head and means for inducing suction through the suction cup.

11. The apparatus as defined in claim 10 wherein the first vacuum source provides a first level of suction to the cutting head and the means for inducing suction through the suction cup comprises a second vacuum source that provides a second level of suction, the second level of suction lower than the first level of suction.

12. The apparatus as defined in claim 1 wherein the handpiece is discarded after a single use.

13. The apparatus as defined in claim 1 wherein the handpiece further comprises a drive tube coupled between the drive cable and the cutting head, the drive tube comprising:
    a rigid proximal portion;
    a rigid distal portion; and
    a flexible drive coupling disposed between the rigid proximal portion and the rigid distal portion.

14. The apparatus as defined in claim 1 further comprising means for advancing the cutting head at high speed in a distal direction.

15. The apparatus as defined in claim 1 further comprising means, disposed on the shaft, for viewing the cutting head when the articulation region is articulated.

16. Apparatus for forming a channel in tissue, the apparatus comprising:
    a controller housing a linear motor and a first vacuum source;
    a handpiece comprising:
        a body,
        a shaft coupled to the body, the shaft having a lumen, a longitudinal axis, and an articulation region;
        a cutting head having a bore coupled to the first vacuum source, a first position wherein the cutting head extends from within the lumen to form a channel in the tissue, tissue severed by the cutting head being aspirated through the bore by the first vacuum source, and a second position wherein the cutting head is retracted within the lumen; and means for articulating the articulation region; and a cable coupling the linear motor and vacuum source, the linear motor causing the cutting head to move the cutting head between the first and second positions.

17. The apparatus as defined in claim 16 further comprising a rotary motor housed within the controller and coupled by the cable to the cutting head to rotate the cutting head.

18. The apparatus as defined in claim 17 wherein the cable comprises a drive cable and the apparatus further comprises a coupling that transmits rotary motion and longitudinal motion from the rotary and linear motors, respectively, to the drive cable.

19. The apparatus as defined in claim 18 wherein the handpiece further comprises a spool coupled between the drive cable and the cutting head, the spool including struts defining apertures that permit tissue aspirated through the bore of the cutting head to pass to a tissue filter.

20. The apparatus as defined in claim 16 wherein the cutting head, in the first position, also experiences motion selected from the group consisting of reciprocatory motion, angular motion or vibrational motion.

21. The apparatus as defined in claim 16 further comprising means for stabilizing the cutting head in contact with the tissue.

22. The apparatus as defined in claim 21 wherein the means for stabilizing comprises a suction cup disposed on the shaft near the cutting head and a second vacuum source housed in the controller that induces suction through the suction cup.

23. The apparatus as defined in claim 16 wherein the handpiece and cable are discarded after a single use.

24. The apparatus as defined in claim 18 wherein the handpiece further comprises a drive tube coupled between the drive cable and the cutting head, the drive tube comprising:

a rigid proximal portion;

a rigid distal portion; and a flexible drive coupling disposed between the rigid proximal portion and the rigid distal portion.

25. The apparatus as defined in claim 16 further comprising means for advancing the cutting head at high speed in a distal direction.

26. The apparatus as defined in claim 16 further comprising means, disposed on the shaft, for viewing the cutting head when the articulation region is articulated.

* * * * *